United States Patent [19]
Lutz et al.

[11] Patent Number: 5,349,101
[45] Date of Patent: Sep. 20, 1994

[54] PROCESS FOR THE PREPARATION OF SECONDARY ALKYL SULFATE-CONTAINING SURFACTANT COMPOSITIONS

[75] Inventors: Eugene F. Lutz; David K. Schisla; Robert S. Tomaskovic, all of Houston; Timothy D. Hoewing, Richmond, all of Tex.

[73] Assignee: Shell Oil Company, Houston, Tex.

[21] Appl. No.: 994,022

[22] Filed: Dec. 21, 1992

Related U.S. Application Data

[63] Continuation-in-part of Ser. No. 890,056, May 28, 1992, abandoned.

[51] Int. Cl.$^5$ .............. C07C 305/12; C11D 1/14; C11D 1/29; C11D 11/04; C06M 13/262
[52] U.S. Cl. .................................. 558/36; 558/39; 558/43; 252/8.75; 252/21; 252/89.1; 252/174; 252/353; 252/548; 252/174.21
[58] Field of Search ............... 252/548, 674.21, 89.1, 252/8.75, 174.21, 353; 558/43, 36, 39

[56] References Cited

U.S. PATENT DOCUMENTS

| | | | |
|---|---|---|---|
| 2,094,546 | 9/1937 | Lyons | 558/43 X |
| 2,640,070 | 5/1953 | Dahmen | 558/43 X |
| 2,945,818 | 7/1960 | Costine et al. | 252/548 X |
| 3,234,258 | 2/1966 | Morris | 252/548 X |
| 3,676,523 | 7/1972 | Mason | 252/548 X |
| 3,681,424 | 8/1972 | Bloch et al. | 252/548 |
| 3,686,351 | 8/1972 | Mason | 558/43 X |
| 3,737,475 | 6/1973 | Mason | 558/43 X |
| 3,825,615 | 7/1974 | Lutz | 558/43 X |
| 3,893,940 | 7/1975 | Ohogoshi et al. | 252/353 |
| 4,020,121 | 4/1977 | Kister et al. | 558/43 |
| 4,052,342 | 10/1977 | Fernley et al. | 252/548 |
| 4,088,598 | 5/1978 | Williams | 252/541 |
| 4,226,797 | 10/1980 | Bakker et al. | 558/43 |
| 4,474,678 | 10/1984 | Lutz et al. | 252/174.21 |
| 4,544,493 | 10/1985 | Silvis | 252/89.1 |
| 4,857,213 | 8/1989 | Caswell et al. | 252/8.75 |
| 5,075,041 | 6/1990 | Lutz | 252/548 |

FOREIGN PATENT DOCUMENTS

| | | | |
|---|---|---|---|
| 1468825 | 1/1969 | Fed. Rep. of Germany | 558/43 |
| 884656 | 12/1961 | United Kingdom | 252/548 |
| 1194862 | 6/1970 | United Kingdom | 558/43 |
| 1585030 | 5/1978 | United Kingdom | 558/43 |

OTHER PUBLICATIONS

Asinger, "The Hydration of Olefins to Alcohols," Mono-olefins: Chemistry and Technology, 1968, pp. 689–704.

*Primary Examiner*—Floyd D. Higel
*Attorney, Agent, or Firm*—Pamela J. McCollough

[57] ABSTRACT

This invention relates to solid secondary alkyl sulfate-containing surface active compositions which are formed by crystallization and which contain at least about 80 percent by weight of secondary alkyl sulfate. These compositions are substantially free of unreacted organic matter and water. The invention further relates to a process for preparing these solid secondary alkyl sulfate-containing compositions.

32 Claims, No Drawings ic acid-containing solution with a base
PROCESS FOR THE PREPARATION OF SECONDARY ALKYL SULFATE-CONTAINING SURFACTANT COMPOSITIONS This is a continuation-in-part of co-pending application Ser. No. 890,056, filed May 2, 1992, abandoned.

FIELD OF THE INVENTION

This invention relates to solid secondary alkyl sulfate-containing surfactant compositions and to a process for preparing the compositions.

BACKGROUND OF THE INVENTION

In conventional practice, secondary alkyl sulfates have been prepared by reaction of olefins or alcohols with sulfuric acid followed by neutralization of the intermediate secondary alkyl sulfuric acid with aqueous base, usually sodium hydroxide. The process is complicated by incomplete reaction of the starting olefin or alcohol and by formation of dialkyl sulfates which saponify during the neutralization step, noted above, to equal molar amounts of secondary alkyl sulfate and secondary alcohol.

Unreacted olefin and secondary alcohol, which can amount to 50% by weight or more of the starting olefin, are generally removed from the secondary alkyl sulfate by a process of extraction with an organic solvent as described in U.S. Pat. No. 4,175,092. The extraction process can be complicated by the formation of undesirable emulsions and gels as well as by the dissolution of some of the extracting solvent in the aqueous secondary alkyl sulfate phase. Extracting solvents frequently have objectionable odors and must be removed from the aqueous surfactant solution, an operation which can be accompanied by severe foaming difficulties. When extraction is complete, the concentration of secondary alkyl sulfate in water is generally in the range of 20–40% by weight (F. Asinger, *Mono-Olefins: Chemistry and Technology*, 1968, pp. 689–694).

It would therefore be advantageous to have solid secondary alkyl sulfate-containing surfactant compositions which are substantially free of water and unreacted organic matter, thus allowing maximum handling flexibility.

A process for preparing surfactant compositions has been found in which secondary alkyl sulfates derived from olefins and/or alcohols can be generated in a manner such that the secondary alkyl sulfate-containing product is a solid which can be used as a surfactant and/or a detergent composition which is particularly suitable for household applications.

SUMMARY OF THE INVENTION

This invention relates to a process for preparing a solid secondary alkyl sulfate-containing surface active composition which comprises contacting a detergent range alkyl sulfuric acid-containing solution and a nonionic organic liquid diluent with a base in aqueous solution, heating to saponify and to remove substantially all of the water from the mixture, cooling to crystallize a solid secondary alkyl sulfate-containing surface active composition from the mixture, and recovering and drying the crystallized solid secondary alkyl sulfate-containing surface active composition.

The invention further relates to solid secondary alkyl sulfate-containing surface active compositions prepared by crystallization which are substantially free of water and unreacted organic matter and which comprise at least about 80 percent by weight of secondary alkyl sulfate.

DESCRIPTION OF THE PREFERRED EMBODIMENTS

The invention provides solid secondary alkyl sulfate-containing surfactant compositions as well as a process for preparing solid secondary alkyl sulfate-containing surfactant compositions which are substantially free of unreacted organic matter (UOM) and water. These solid surface active compositions are prepared by contacting a detergent range alkyl sulfuric acid-containing solution with a base in aqueous solution, heating to remove substantially all of the water from the mixture, cooling in the presence of a nonionic organic liquid diluent to crystallize a solid secondary alkyl sulfate-containing surface active composition from the mixture, and recovering and drying the crystallized secondary alkyl sulfate-containing product, thereby producing a solid secondary alkyl sulfate-containing surfactant composition which is typically a free flowing powder, which is anhydrous and which is substantially free of diluents.

The present invention therefore relates to solid secondary alkyl sulfate-containing surface active compositions, typically free flowing powders, which are substantially free of unreacted organic matter and water, prepared by a process which in its broadest aspect comprises: a) preparing a detergent range alkyl sulfuric acid-containing solution, b) contacting a detergent range alkyl sulfuric acid-containing solution with a base in aqueous solution, c) heating to saponify and to remove substantially all of the water from the mixture, d) cooling the product of step c) in the presence of a nonionic organic liquid diluent to crystallize a solid secondary alkyl sulfate-containing surface active composition from the mixture, and e) recovering and drying the crystallized solid secondary alkyl sulfate-containing surface active composition.

Specifically, the present process for preparing solid secondary alkyl sulfate-containing surface active compositions which are substantially free of unreacted organic matter and water comprises the steps of: a) sulfating a reactant selected from the group consisting of detergent range olefins, detergent range alcohols and mixtures thereof, b) neutralizing the sulfation product of step a) with a base in aqueous solution, c) saponifying the product of step b), d) crystallizing the product of step c), and e) recovering and drying the secondary alkyl sulfate-containing product from the product of step d), wherein a nonionic organic liquid diluent is added prior to step d). In the foregoing process, the nonionic organic liquid diluent can be added during the sulfation step, following the sulfation step, or during the neutralization or saponification steps, provided the diluent is substantially inert in the particular step in which it is added. It is not critical at what point the nonionic organic liquid diluent is added as long as the diluent is present prior to crystallization. The portion of the reaction mixture which remains following the step in which the crystallized secondary alkyl sulfate-containing product is recovered can be recycled, if desired.

As used herein, the phrase "substantially free of unreacted organic matter and water" refers to compositions which contain less than about 10 percent by weight, preferably less than about 5 percent by weight, of unreacted organic matter and less than about 5 percent by weight, preferably less than about 2 percent by weight, of water.

The detergent range alkyl sulfuric acid-containing solution in step a) of the present process can be prepared by sulfation of detergent range olefins, detergent range alcohols or a mixture of detergent range olefins and alcohols. In a preferred embodiment, the detergent range alkyl sulfuric acid-containing solution is prepared by the sulfation of detergent range olefins or by the sulfation of a mixture of detergent range olefins and detergent range alcohols.

The detergent range olefins which are suitable for use in the preparation of the detergent range alkyl sulfuric acid-containing solution are olefins containing from about 8 to about 22 carbon atoms. These olefins can be alpha olefins or internal olefins and they may be linear or branched, but are preferably linear or lightly branched. Single cut olefins or mixtures of olefins may also be used. In a particularly preferred embodiment, the olefin contains from about 12 to about 18 carbon atoms.

Preferred olefins for use in the preparation of the alkyl sulfuric acid-containing solution for the practical reason of availability are the commercial olefin products in the $C_8$ to $C_{22}$ range. While commercial production of such olefins may be carried out by the cracking of paraffin wax, commercial production is more commonly accomplished by the oligomerization of ethylene using procedures well known in the art. The resulting oligomerization products are substantially of linear structure and thus products are substantially of linear structure. Commercial olefin products manufactured by ethylene oligomerization are marketed in the U.S. by Shell Chemical Company under the trademark NEODENE and by Ethyl Corporation as Ethyl Alpha-Olefins. Specific procedures for preparing suitable linear olefins from ethylene are described in U.S. Pat. Nos. 3,676,523, 3,686,351, 3,737,475, 3,825,615 and 4,020,121, the teachings of which are incorporated herein by reference. While most of such olefin products are comprised largely of alpha-olefins, higher linear internal olefins are also commercially produced, for example, by the chlorinationdehydrochlorination of paraffins, by paraffin dehydrogenation, and by isomerization of alpha-olefins. Linear internal olefin products in the $C_8$ to $C_{22}$ range are marketed by Shell Chemical Company and by Liquichemica Company. These commercial products, whether predominantly internal or alpha-olefins typically contain about 70 percent by weight or more, most often about 80 percent by weight or more, linear mono-olefins in a specified carbon number range (e.g., $C_{10}$ to $C_{12}$, $C_{11}$ to $C_{15}$, $C_{12}$ to $C_{13}$, $C_{15}$ to $C_{18}$, etc.), the remainder of the product being olefin of other carbon number or carbon structure, diolefins, paraffins, aromatics, and other impurities resulting from the synthesis process. Olefins in the $C_{12}$ to $C_{18}$ range are considered most preferred for use in the instant invention.

The detergent range alcohols which are suitable for use in the preparation of the detergent range alkyl sulfuric acid-containing solution are alcohols containing from about 8 to about 22 carbon atoms. Acyclic aliphatic alcohols (alcohols) having from about 9 to about 18 carbon atoms form a preferred class of reactants, particularly the secondary alcohols, as secondary alcohols make up a portion of the potential recycle stream in the present process, although primary alcohols can also be utilized. When primary alcohols are utilized in combination with olefins and/or secondary alcohols, the product obtained will be a mixture of primary alkyl sulfates and secondary alkyl sulfates. As a general rule, the alcohols may be of branched or straight chain structure, although alcohol reactants in which greater than about 50 percent, more preferably greater than about 60 percent, and most preferably greater than about 70 percent of the molecules are of linear (straight-chain) carbon structure are preferred.

When mixtures of detergent range olefins and detergent range alcohols are used in the preparation of the detergent range alkyl sulfuric acid-containing solution, the mixture suitably comprises from about 40 percent to about 90 percent detergent range olefins and from about 10 percent to about 60 percent detergent range alcohols. A preferred mixture includes from about 60 percent to about 80 percent detergent range olefins and from about 20 percent to about 40 percent detergent range alcohols.

The sulfating agents suitable for use in preparing the alkyl sulfuric acid-containing solution in step a) include those compounds capable of forming the carbon to oxygen to sulfur bonds necessary for the formation of an alkyl sulfate. The particular sulfating agents used are typically a function of the compounds to be sulfated. These sulfating agents are known in the art and include sulfuric acid or sulfuric acid salts for the sulfation of olefins, and sulfur trioxide, chlorosulfonic acid or oleum for the sulfation of alcohols. In a preferred embodiment, the alkyl sulfuric acid-containing solution is derived from the sulfation of detergent range olefins or a mixture of detergent range olefins and detergent range alcohols and the sulfating agent is concentrated sulfuric acid.

When concentrated sulfuric acid is used to sulfate detergent range olefins or a mixture of detergent range olefins and detergent range alcohols, the concentrated sulfuric acid is typically from about 75 percent by weight to about 100 percent by weight, preferably from about 85 percent by weight to about 98 percent by weight, in water. Suitable amounts of sulfuric acid are generally in the range of from about 0.3 moles to about 1.3 moles of sulfuric acid per mole of olefin and/or alcohol, preferably from about 0.4 moles to about 1.0 mole of sulfuric acid per mole of olefin and/or alcohol.

The sulfation reaction which results in the alkyl sulfuric acid-containing solution is typically carried out at temperatures in the range of from about $-20°$ C. to about 50° C., preferably from about 5° C. to about 40° C., and at pressures in the range of from about 1 atmosphere to about 5 atmospheres, preferably from about 1 atmosphere to about 2 atmospheres, and more preferably, about 1 atmosphere. Suitable residence times for the sulfation reaction range from a few minutes to several hours, preferably from about 2 minutes to about 10 hours and more preferably, from about 5 minutes to about 3 hours.

The sulfation reaction for a detergent range olefin may be illustrated by the following equation:

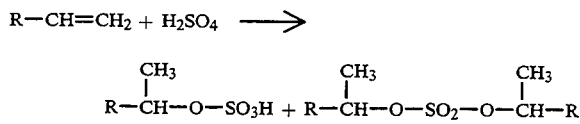

wherein R is an alkyl group having from about 6 to about 20 carbon atoms. The sulfation reaction results in an alkyl sulfuric acid-containing solution. As used herein, the term "alkyl sulfuric acid-containing solution" is used to refer to all of the products of the sulfation reaction which include primarily monoalkyl sulfuric acids and dialkyl sulfates along with unreacted olefin and unreacted sulfuric acid.

In one embodiment, the alkyl sulfuric acid-containing solution may, prior to the contact with an aqueous solution of a base in step b) or prior to neutralization, be subjected to deacidification for the partial or substantially complete removal of any unreacted sulfuric acid or any other unreacted sulfating agent. Suitable deacidification procedures include washing the sulfation reaction product with water or an acid such as sulfuric acid having a concentration of from about 75 percent by weight to about 90 percent by weight, preferably from about 80 percent by weight to about 85 percent by weight, in water. The deacidification is typically carried out at the same temperature at which the sulfation reaction is carried out. While it is not critical that the alkyl sulfuric acid-containing solution be subjected to deacidification, in a preferred embodiment, the alkyl sulfuric acid-containing solution is deacidified by the addition of small amounts of sulfuric acid thereto in order to remove as much unreacted sulfating agent as possible.

The nonionic organic liquid diluent in the present process is typically an aliphatic or aromatic hydrocarbon, but can be any composition which will permit secondary alkyl sulfate precipitation. As used herein, the term "nonionic organic liquid diluent" is used to refer to a composition having characteristics such that the secondary alkyl sulfate product precipitates from solution. The nonionic organic liquid diluent, if inert to the specific step in the reaction sequence, may be added along with the detergent range olefins and/or alcohols at the beginning of the sulfation step, at any point during the sulfation step, after the sulfation reaction is completed, following the deacidification step, or, it may be contacted with the alkyl sulfuric acid-containing solution during contact of the solution with the aqueous solution of base. Alternatively, the nonionic organic liquid diluent may be added at more than one of the above-mentioned places in the process, provided it is substantially inert in the place in which it is added. In a preferred embodiment, the nonionic organic liquid diluent is added to the alkyl sulfuric acid-containing solution following the sulfation step. Suitable nonionic organic liquid diluents include heptane, toluene, isooctane, nonane and mixtures thereof, with preference being given to heptane and isooctane, particularly heptane. While not wishing to be bound by any particular theory, it is believed that the function of the nonionic organic liquid diluent in the present process is to provide a medium in which unreacted organic matter is soluble and secondary alkyl sulfate, at least in part, is not.

The alkyl sulfuric acid-containing solution and nonionic organic liquid diluent are contacted with an aqueous solution of a base in order to neutralize the alkyl sulfuric acid portion of the sulfuric acid-containing solution to form the corresponding sulfuric acid salts.

The neutralization reaction is accomplished using an aqueous solution of one or more bases such as ammonium or alkali metal or alkaline earth metal hydroxides or carbonates or bicarbonates. Suitable bases include sodium hydroxide, sodium carbonate, potassium hydroxide, calcium hydroxide and the like, with sodium hydroxide or potassium hydroxide being the preferred base. The concentration of the aqueous solution of base is suitably from about 10 percent by weight to about 85 percent by weight base, preferably from about 15 percent by weight to about 75 percent by weight, and more preferably from about 20 percent by weight to about 50 percent by weight, in water. In a preferred embodiment, the base utilized is sodium hydroxide or potassium hydroxide, and the concentration of the aqueous solution of base is from about 10 percent by weight to about 75 percent by weight base, preferably from about 20 percent by weight to about 50 percent by weight, in water. Generally, an amount of base in excess of the amount required to neutralize the alkyl sulfuric acids and saponify the dialkyl sulfates is used. Suitable amounts of base are generally in the range of from about 1.2 moles to about 1 mole of base per equivalent of sulfuric acid, alkyl sulfuric acid and dialkyl sulfate, and preferably in the range of from about 1.1 moles to about 1.0 mole of base.

The neutralization procedure can be carried out over a wide range of temperatures and pressures. Typically, the neutralization procedure is carried out at a temperature in the range of from about 20° C. to about 65° C., and a pressure in the range of from about 1 atmosphere to about 2 atmospheres. The neutralization time is typically in the range of from about 0.2 hours to about 1.0 hours.

Following the contact in step b) of the alkyl sulfuric acid-containing solution and the nonionic organic liquid diluent with an aqueous solution of a base to effect neutralization, the product of step b), is heated in step c) to a temperature in the range of from about 70° C. to about 115° C., preferably from about 80° C. to about 105° C. in order to effect saponification or hydrolysis of the dialkyl sulfates to form alkyl sulfuric acid salts and secondary alcohols and remove substantially all of the water from the product of step b). In this step, water is azeotropically distilled to remove a liquid containing a water phase and a nonionic organic liquid diluent phase. The nonionic organic liquid diluent phase is returned to the reaction vessel and the water phase is discarded. This step is typically carried out using a Dean Stark trap or other similar device.

The saponification procedure can be carried out over a wide range of temperature and pressures. The saponification procedure is typically carried out at a temperature in the range of from about 80° C. to about 105° C. and a pressure of from about 1 atmosphere to about 2 atmospheres. The saponification reaction is generally carried out over a time period ranging from about 0.25 hours to about 5.0 hours.

The neutralization and saponification reactions may be illustrated by the following equations:

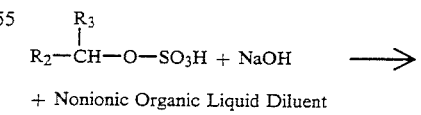

+ Nonionic Organic Liquid Diluent

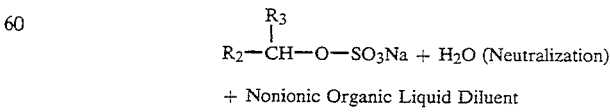

+ Nonionic Organic Liquid Diluent

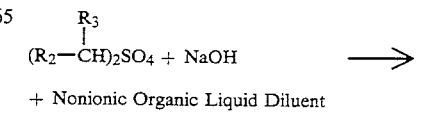

+ Nonionic Organic Liquid Diluent

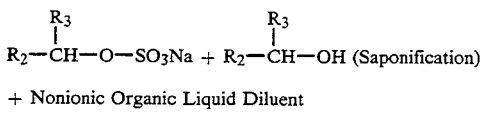

+ Nonionic Organic Liquid Diluent wherein $R_2$ and $R_3$ are alkyl groups having from about 1 to about 20 carbon atoms.

Following saponification and removal of substantially all of the water, the resulting product is then cooled to a temperature in the range of from about 20° C. to about 85° C. to effect crystallization of the solid secondary alkyl sulfate from the saponified product of step c). The cooling step generally takes place over a period of about 0.25 hours to about 18 hours, preferably about 0.5 hours to about 16 hours, although both shorter and longer time periods are also acceptable. During the cooling step, the solubility of secondary alkyl sulfate is further reduced and additional secondary alkyl sulfate solids are formed.

The crystallized secondary alkyl sulfate product is then recovered and dried as solid secondary alkyl sulfate-containing composition. The secondary alkyl sulfate crystals can be recovered by filtration or centrifugation. The crystallized secondary alkyl sulfate-containing product is typically dried at temperatures in the range of from about 40° C. to about 80° C. using nitrogen-swept vacuum or other conventional drying means. Either prior to or following drying, the crystals may be subjected to washing with the particular nonionic organic liquid diluent utilized or with any other conventional washing agent in order to increase the purity of the secondary alkyl sulfate-containing product. In a preferred embodiment, the crystals are washed with chilled water, i.e., water having a temperature of from about 2° C. to about 20° C., preferably from about 5° C. to about 10° C., in order to remove at least a portion of the sodium sulfate and thus produce a secondary alkyl sulfate-containing product having less than about 5 percent by weight, preferably less than about 2 percent by weight, sodium sulfate.

The remainder of the product of step e) which contains unreacted starting material, secondary alcohol, and nonionic organic liquid diluent, as well as some uncrystallized secondary alkyl sulfate, may be recycled. Alternatively, the uncrystallized secondary alkyl sulfate may be removed from the product of step e), if desired, prior to recycle. In addition, if desired, the secondary alcohol can be separated from the unreacted starting material by means recognized by those skilled in the art such as, for example, distillation.

The process of the present invention may be carried out in a batch mode or in a continuous operation.

The solid secondary alkyl sulfate product produced contains at least about 80 percent by weight to about 99 percent by weight, preferably about 88 percent by weight to about 99 percent by weight of secondary alkyl sulfate. The product generally contains some residual level of sodium sulfate. The product typically contains less than about 12 percent by weight, preferably less than about 9 percent by weight, sodium sulfate.

The surfactant compositions of the invention can be utilized in a variety of detergent applications. The surfactant compositions can be blended with solid detergent components such as, for example, sodium carbonate, in order to form dry detergent powders. The surfactant compositions can also be added to water or vice versa in order to form liquid detergents.

The ranges and limitations provided in the instant specification and claims are those which are believed to particularly point out and distinctly claim the present invention. It is, however, understood that other ranges and limitations which perform substantially the same function in substantially the same manner to obtain the same or substantially the same result are intended to be within the scope of the instant invention as defined by the instant specification and claims.

The invention will be described below by the following examples which are provided for purposes of illustration and are not to be construed as limiting the invention.

ILLUSTRATIVE EMBODIMENTS

EXAMPLE 1

To a 3-necked flask equipped with a paddle stirrer, thermometer, and addition flask topped with a nitrogen blanket was added 196.01 grams of NEODENE 14 (at least 95% wt. $C_{14}$ and at least 94% wt. normal alpha olefin) (NEODENE is a trademark of Shell Chemical Company). After cooling in an ice bath to 9° C., 81.88 grams of 95% sulfuric acid was added with good agitation at such a rate that the temperature did not exceed 19° C. When the addition of sulfuric acid was complete, 80.00 grams of cold heptane was added, followed by the addition of 200.09 grams of 82% sulfuric acid. After fifteen minutes of good agitation at 12°–14° C., stirring was stopped and the mixture transferred to a separatory funnel. When phase separation was complete at 20° C., the lower phase was removed and weighed 212.25 grams. The upper phase, which weighed 345.00 grams, was titrated for acidity (1.166 meq (milliequivalents)/g (gram)) and then added to 68.04 grams of 50% sodium hydroxide and 60.09 grams of heptane in a 4-necked flask equipped with a paddle stirrer, thermometer, a Dean Stark trap with a nitrogen blanket, and an addition flask. The temperature in the reaction flask rose from about 24° C. to 70° C. during acid neutralization. When acid addition was complete, the addition flask was replaced with a nitrogen blanketed Dean Stark trap and the reactor heated to azeotrope water from the reaction mixture. Water began to azeotrope at a reactor temperature of about 95° C. After 38.37 grams of water had distilled and the reaction temperature had risen to 106° C., heating was discontinued and the heptane in the Dean Stark traps was returned to the reactor.

On cooling overnight to room temperature, the reactor contents were transferred to 2 centrifuge tubes with the aid of an additional 53.51 grams of heptane. The solid was separated from the mother liquor by centrifuging at 1500 revolutions per minute (rpm) for fifteen minutes at 25° C. The mother liquor was decanted from the centrifuge tubes and the two solids were slurried with 80 grams of pentane each. Centrifugation was performed again as described above followed by mother liquor decantation and reslurry of the solid in pentane. This procedure was repeated two more times and then the solid product was transferred to a tared dish and dried at 63° C. in a nitrogen-swept vacuum oven at 8 inches of mercury. The dried secondary tetradecyl sulfate weighed 145.63 grams. Analysis showed the recovered product to be 92.8% by weight anionic surfactant, 5.5% by weight sodium sulfate and 1.6% by weight sodium hydroxide. The product yield was 42.8% mole (% m), basis starting olefin. The results are presented in Table I.

EXAMPLE 2

Example 2 was carried out in a manner similar to Example 1 except that NEODENE 16 (at least 92% wt. $C_{16}$ and at least 94% wt. normal alpha olefin) was used and toluene rather than heptane was utilized. Toluene (160 grams) was added after neutralization with 50% wt. sodium hydroxide. The results are presented in Table I.

EXAMPLE 3

Example 3 was carried out in a manner similar to Example 1 except that the sulfuric acid to NEODENE 16 ratio was 0.6 mole/mole, the 82% acid wash was omitted and isooctane (208 grams) rather than heptane was utilized. The results are presented in Table I.

EXAMPLE 4

Example 4 was carried out in a manner similar to Example 1 except that a mixture of internal olefins (approximate composition: 4% wt. $C_{14}$; 47.6% wt. $C_{15}$; 34.0% wt. $C_{16}$; 11.9% wt. $C_{17}$ and 2.5% wt. $C_{18}$) was used as the olefin reactant. The internal olefins were distilled from NEODENE 1518 (approximate distribution: 1.8% wt. $C_{14}$; 24.7% wt. $C_{15}$; 26.1% wt. $C_{16}$; 24.5% wt. $C_{17}$; 18.3% wt. $C_{18}$ and 4.6% wt. $C_{19}$). The results are presented in Table I.

EXAMPLE 5

To a resin kettle equipped with a paddle stirrer, thermometer, and addition flask topped with a nitrogen blanket was added 628.3 grams of NEODENE 14 (at least 95% wt. $C_{14}$ and at least 94% wt. normal alpha olefin). After cooling to 14° C., 197.5 grams of 95% sulfuric acid was added with good agitation at such a rate that the temperature did not exceed 25° C. When the addition of sulfuric acid was complete, 315 grams of heptane was added and the entire solution was then added to 185.5 grams of 50% wt. sodium hydroxide and 370.23 grams of distilled water in a 4-necked flask equipped with a paddle stirrer, thermometer, and Dean Stark traps with nitrogen blankets. The temperature in the reaction flask rose from about 34° C. to 68° C. during acid neutralization. When acid addition was complete, an additional 10.21 grams of 50% wt. sodium hydroxide and 945 grams of heptane were added to the reaction flask. The reactor was heated and water began to azeotrope at a reactor temperature of about 84° C. After 471.15 grams of water had distilled and the reaction temperature had risen to 100° C., heating was discontinued and the heptane in the Dean Stark traps was weighted and then discarded.

On cooling overnight to room temperature, the solid reaction product was recovered by filtration through two Buchner funnels fitted with Whatman #4 paper. The solid was washed with 3940 grams of heptane, after which the filter cakes were dried in a nitrogen-swept vacuum oven at 70° C. The dried secondary tetradecyl sulfate weighed 456.14 grams. Analysis showed the recovered product to be 90.6% by weight anionic surfactant, 7.6% by weight sodium sulfate and 0.3% by weight sodium hydroxide. The product yield was 40.9% m, basis starting olefin. The results are presented in Table I.

EXAMPLE 6

Example 6 was carried out in a manner similar to Example 5 except that a mixture of internal olefins (as described in Example 4 above) and NEODENE 16 (as described in Example 2 above) in a ratio of 60% wt. to 40% wt., respectively, was used as the olefin reactant. The sulfation reaction was monitored until acidity was constant and then neutralization was performed in the usual manner. The results are presented in Table I.

EXAMPLE 7

Example 7 was carried out in a manner similar to Example 5 except that a mixture of 84.00 grams of NEODENE 16 (as described in Example 2 above) and 30.26 grams of secondary hexadecanol (s-hexadecanol) (88% wt. 2-ol and 12% wt. 3-ol) was sulfated with 25.65 grams of 95% sulfuric acid. When sulfation was complete, as determined by titration, the reaction sequence was completed as described in Example 5. The results are presented in Table I.

TABLE I

| Example No. | Olefin and/or Alcohol Reactant | Acid/Olefin and/or Alcohol Ratio (mole/mole) | Diluent | Secondary Alkyl Sulfate Recovered as Solid (% m) | Secondary Alkyl Sulfate Purity (% wt.) |
| --- | --- | --- | --- | --- | --- |
| 1 | NEODENE 14 | 0.8 | Heptane | 42.8 | 92.8 |
| 2 | NEODENE 16 | 0.8 | Toluene | 43.8 | 89.1 |
| 3 | NEODENE 16 | 0.6 | Isooctane | 44.8 | 82.4 |
| 4 | Internal Olefin ($C_{14}/C_{18}$) | 0.8 | Heptane | 18.8 | 87.4 |
| 5 | NEODENE 14 | 0.6 | Heptane | 40.9 | 90.6 |
| 6 | Internal Olefin: NEODENE 16 (60:40) | 0.6 | Heptane | 21.2 | 99 |
| 7 | NEODENE 16: s-hexadecanol (74% wt.: 26% wt.) | 0.5 | Heptane | 25.1 | 97.1 |

What is claimed is:

1. A process for preparing a solid secondary alkyl sulfate-containing surface active composition which comprises:
   a) preparing a detergent range alkyl sulfuric acid-containing solution,
   b) contacting said detergent range alkyl sulfuric acid-containing solution with a base in aqueous solution, c) heating the product of step b) to saponify dialkyl sulfate and to remove substantially all of the water from the mixture, d) cooling the product of step c) in the presence of a nonionic organic liquid diluent to crystallize a solid secondary alkyl sulfate-containing surface active composition from the mixture, and e) recovering and drying the crystallized solid secondary alkyl sulfate-containing surface active composition.

2. The process of claim 1 wherein said detergent range alkyl sulfuric acid-containing solution is prepared by sulfating a reactant selected from the group consisting of detergent range olefins, detergent range alcohols and mixtures thereof, with a sulfating agent.

3. The process of claim 1 wherein the nonionic organic liquid diluent is selected from the group consisting of aliphatic hydrocarbons, aromatic hydrocarbons and mixtures thereof.

4. The process of claim 3 wherein the nonionic organic liquid diluent in step c) is selected from the group consisting of heptane, toluene, isooctane, nonane, and mixtures thereof.

5. The process of claim 1 wherein the base in step b) is selected from ammonium, alkali metal or alkaline earth metal hydroxides, carbonates or bicarbonates.

6. The process of claim 5 wherein said base is selected from the group consisting of sodium hydroxide, potassium hydroxide and mixtures thereof.

7. The process of claim 1 wherein said base in aqueous solution comprises from about 10 percent by weight to about 85 percent by weight of base in water.

8. The process of claim 7 wherein said base in aqueous solution comprises from about 20 percent by weight to about 50 percent by weight of base in water.

9. The process of claim 1 wherein said solid secondary alkyl sulfate-containing surface active composition recovered in step e) contains from about 80 percent by weight to about 99 percent by weight secondary alkyl sulfate.

10. The process of claim 9 wherein said solid secondary alkyl sulfate-containing surface active composition recovered in step e) contains from about 88 percent by weight to about 99 percent by weight secondary alkyl sulfate.

11. The process of claim 1 wherein prior to drying, the crystallized solid secondary alkyl sulfate-containing surface active composition is washed with chilled water.

12. The process of claim 1 wherein following drying, the crystallized solid secondary alkyl sulfate-containing surface active composition is washed with chilled water.

13. A process for preparing secondary alkyl sulfate-containing surface active compositions substantially free of unreacted organic matter and water, which process comprises:

a) sulfating a reactant selected from the group consisting of detergent range olefins, detergent range alcohols and mixtures thereof, b) neutralizing the sulfation product of step a) with a base in aqueous solution, c) saponifying the product of step b), d) crystallizing the product of step c), and e) recovering and drying the secondary alkyl sulfate-containing product from the product of step d), wherein a nonionic organic liquid diluent is added prior to step d).

14. The process of claim 13 wherein said reactant is a detergent range olefin having from about 12 to about 18 carbon atoms.

15. The process of claim 13 wherein said sulfating step is carried out using concentrated sulfuric acid having a concentration of from about 75 percent by weight to about 100 percent by weight in water.

16. The process of claim 13 wherein said sulfating step is carried out at a temperature in the range of from about 5° C. to about 40° C. and a pressure in the range of from about 1 atmosphere to about 2 atmospheres.

17. The process of claim 13 wherein following step a), the product of step a) is subjected to deacidification by water washing.

18. The process of claim 13 wherein said base in step b) is selected from ammonium, alkali metal or alkaline earth metal hydroxides, carbonates or bicarbonates.

19. The process of claim 18 wherein said base is selected from the group consisting of sodium hydroxide, potassium hydroxide and mixtures thereof.

20. The process of claim 13 wherein said base in aqueous solution comprises from about 10 percent by weight to about 85 percent by weight base in water.

21. The process of claim 20 wherein said base in aqueous solution comprises from about 20 percent by weight to about 50 percent by weight base in water.

22. The process of claim 13 wherein said neutralization in step b) is carried out at temperatures in the range of from about 20° C. to about 65° C. and pressures in the range of from about 1 atmosphere to about 2 atmospheres.

23. The process of claim 13 wherein said saponification in step c) is carried out at a temperature in the range of from about 80° C. to about 105° C. and a pressure of from about 1 atmosphere to about 2 atmospheres.

24. The process of claim 13 wherein the nonionic organic liquid diluent is selected from the group consisting of aliphatic hydrocarbons, aromatic hydrocarbons and mixtures thereof.

25. The process of claim 24 wherein the nonionic organic liquid diluent is selected from the group consisting of heptane, toluene, isooctane, nonane, and mixtures thereof.

26. The process of claim 13 wherein the nonionic organic liquid diluent is added in step a).

27. The process of claim 13 wherein the nonionic organic liquid diluent is added in step b).

28. The process of claim 13 wherein the nonionic organic liquid diluent is added in step c).

29. The process of claim 13 wherein prior to drying, the crystallized solid secondary alkyl sulfate-containing surface active composition is washed with chilled water.

30. The process of claim 13 wherein following drying, the crystallized solid secondary alkyl sulfate-containing surface active composition is washed with chilled water.

31. The process of claim 13 wherein said product recovered in step e) contains from about 80 percent by weight to about 99 percent by weight secondary alkyl sulfate.

32. The process of claim 31 wherein said product recovered in step e) contains from about 88 percent by weight to about 99 percent by weight secondary alkyl sulfate.

* * * * *